(12) United States Patent
Hilliard, Jr. et al.

(10) Patent No.: US 7,749,951 B2
(45) Date of Patent: Jul. 6, 2010

(54) ENHANCED OIL DELIVERY FROM STRUCTURED SURFACTANT FORMULATIONS

(75) Inventors: Peter R. Hilliard, Jr., Far Hills, NJ (US); Nadia Soliman, East Brunswick, NJ (US); Peter Haugk, Lincoln Park, NJ (US)

(73) Assignee: Colgate-Palmolive Company, New York, NY (US)

( * ) Notice: Subject to any disclaimer, the term of this patent is extended or adjusted under 35 U.S.C. 154(b) by 0 days.

(21) Appl. No.: 11/668,740

(22) Filed: Jan. 30, 2007

(65) Prior Publication Data

US 2007/0207936 A1 Sep. 6, 2007

(51) Int. Cl.
*C11D 17/00* (2006.01)
(52) U.S. Cl. .................. 510/426; 510/427; 510/433; 510/490; 510/501
(58) Field of Classification Search .............. None
See application file for complete search history.

(56) References Cited

U.S. PATENT DOCUMENTS

| | | | |
|---|---|---|---|
| 4,618,446 A | 10/1986 | Haslop et al. |
| 5,262,079 A | 11/1993 | Kacher et al. |
| 5,556,628 A | 9/1996 | Derian et al. |
| 5,612,307 A | 3/1997 | Chambers et al. |
| 5,650,384 A | 7/1997 | Gordon et al. |
| 5,661,189 A | 8/1997 | Grieveson et al. |
| 5,683,683 A | 11/1997 | Scafidi |
| 5,965,500 A | 10/1999 | Puvvada |
| 6,074,633 A | 6/2000 | Dubief et al. |
| 6,077,816 A | 6/2000 | Puvvada et al. |
| 6,080,707 A | 6/2000 | Glenn et al. |
| 6,080,708 A | 6/2000 | Glenn et al. |
| 6,150,312 A | 11/2000 | Puvvada et al. |
| 6,174,846 B1 | 1/2001 | Villa |
| 6,194,364 B1 | 2/2001 | Glenn, Jr. |
| 6,770,612 B1 | 8/2004 | Hatchman |
| 2003/0180246 A1 | 9/2003 | Frantz et al. |
| 2004/0057920 A1 | 3/2004 | Focht et al. |
| 2004/0092415 A1 | 5/2004 | Focht et al. |
| 2004/0143269 A1 | 7/2004 | Pude et al. |
| 2004/0219119 A1 | 11/2004 | Wei et al. |

(Continued)

FOREIGN PATENT DOCUMENTS

RU 2032726 4/1995

(Continued)

OTHER PUBLICATIONS

Miracare SLB-365 Material Safety Data Sheet (Jan. 29, 2004).

(Continued)

*Primary Examiner*—Necholus Ogden, Jr.
(74) *Attorney, Agent, or Firm*—Michael F. Morgan

(57) ABSTRACT

Described are methods for preparing compositions that include the steps of (a) premixing a cationic guar gum in water; (b) adding a surfactant component to the premix of (a); (c) adding about 1 to about 3 weight % of salt to the mixture obtained in (b); (d) applying shear to the mixture obtained in (c) at a shear rate not exceeding about 20 $sec^{-1}$ to form a spherulite composition; and (f) mixing an oil phase with the spherulite composition. Also included are compositions prepared by this process.

4 Claims, 1 Drawing Sheet

U.S. PATENT DOCUMENTS

| | | | |
|---|---|---|---|
| 2004/0223991 A1 | 11/2004 | Wei et al. | |
| 2004/0234565 A1 | 11/2004 | Stella et al. | |
| 2004/0235693 A1 | 11/2004 | Wei et al. | |
| 2004/0235702 A1 | 11/2004 | Hawkins | |
| 2004/0248748 A1 | 12/2004 | Wei et al. | |
| 2005/0020468 A1 | 1/2005 | Frantz et al. | |
| 2005/0025731 A1 | 2/2005 | Knopf et al. | |
| 2005/0100570 A1 | 5/2005 | Wei et al. | |
| 2005/0124526 A1 | 6/2005 | D'Angelo et al. | |
| 2005/0143268 A1 | 6/2005 | Midha et al. | |
| 2005/0192187 A1 | 9/2005 | Wagner et al. | |
| 2005/0192188 A1 | 9/2005 | Wagner et al. | |
| 2005/0192189 A1 | 9/2005 | Wagner et al. | |
| 2005/0233935 A1 | 10/2005 | Gunn et al. | |
| 2005/0238680 A1 | 10/2005 | Stella et al. | |
| 2005/0239670 A1 | 10/2005 | Stella et al. | |
| 2005/0276768 A1 | 12/2005 | Wei et al. | |
| 2005/0276829 A1 | 12/2005 | Stella et al. | |
| 2006/0040837 A1 | 2/2006 | Frantz et al. | |
| 2006/0135627 A1 * | 6/2006 | Frantz et al. | 516/67 |

FOREIGN PATENT DOCUMENTS

| | | |
|---|---|---|
| WO | WO 97/05857 | 2/1997 |
| WO | WO 2004/026276 | 4/2004 |
| WO | WO 2004/050055 | 6/2004 |

OTHER PUBLICATIONS

Miracare SLB-365 Material Safety Data Sheet (Jul. 20, 2004).
Dove Deep Moisture Body Wash Formula from Product label (undated).
Olay Body Wash Formula from product label (undated).
File History for U.S. Appl. No. 11/207,238.
File History for U.S. Appl. No. 11/687,705.
Presentation under confidentiality from Rhodia on Jan. 14, 2004 titled, Structured Liquids and Structured Formulations.
Formula R-0287-191 under confidentiality from Rhodia on Jan. 28, 2004.
Formulas R-287-185 & -186 under confidentiality from Rhodia on Feb. 18, 2004.
Formulas R-287-156-1A & -2A under confidentiality from Rhodia on Feb. 18, 2004.
Formula R-287-136 under confidentiality from Rhodia on Feb. 18, 2004.
Formula R-0091-200M under confidentiality from Rhodia on Feb. 18, 2004.
Confidential Letter from Seren Frantz at Rhodia to Peter Haugk at Colgate-Palmolive on 5.
Confidential document for "graniness" observed with Jaguar S from Rhodia on Jul. 11, 2004.

* cited by examiner

ENHANCED OIL DELIVERY FROM STRUCTURED SURFACTANT FORMULATIONS

CROSS-REFERENCE TO RELATED APPLICATIONS

This application claims the benefit of U.S. patent application Ser. No. 11/207,238, filed Aug. 19, 2005, which in turn claims priority to U.S. Provisional Patent Application Ser. No. 60/603,125, filed Aug. 19, 2004, the disclosures of each of which are incorporated herein by reference.

BACKGROUND OF THE INVENTION

Body wash products can be very inefficient delivery vehicles for depositing hydrophobic actives and moisturizers on the skin's surface, since most of the hydrophobic actives are rinsed away during the washing process. The majority of body wash products consist of entangled rod-like micelle formulas. Current oil-in-water body wash formulas do not form stable products at high oil concentrations, since the oils and product aqueous base have significantly different densities. Since micellar based body washes can have high viscosities, but not long range structure (substantially larger than the dimensions of the surfactant micelles themselves), products containing high concentrations of oil will be unstable and phase separate with time. One solution to this problem is to use oil-in-water emulsion systems to incorporate oil into surfactant systems. However, these systems can require heat to make, may be unstable at higher oil concentrations, and may result in a significant impairment of cleansing properties at low surfactant concentrations.

Spherulite based formulas with lamellar surfactant phases which form structured systems have been described. Examples include U.S. Pat. Nos. 5,661,189; 5,965,500; and 6,174,846. These spherulite systems are used primarily to enhance the stability of body wash formulas containing significant amounts of emollients and oils through a significant reduction in the rate of diffusion of oil droplets in the surfactant media. Thus, increased concentrations of oils can be incorporated into the products with the potential to delivery higher concentrations to the skin's surface, when compared to rod like micelle formulations.

The rheological behavior of all surfactant solutions, including liquid cleansing solutions, is strongly dependent on the microstructure, i.e., the shape and concentration of micelles or other self-assembled structures in solution. When there is sufficient surfactant to form micelles (concentrations above the critical micelle concentration or CMC), for example, spherical, cylindrical (rod-like) or discoidal micelles may form. As surfactant concentration increases, ordered liquid crystalline phases such as lamellar phase, hexagonal phase or cubic phase may form. The lamellar phase, for example, consists of alternating surfactant bilayers and water layers. These layers are not generally flat but fold to form spherical onion like structures called vesicles or liposomes. The hexagonal phase, on the other hand, consists of long cylindrical micelles arranged in a hexagonal lattice. In general, the microstructure of most personal care products consist of either spherical micelles; rod micelles; or a lamellar dispersion.

As noted above, micelles may be spherical or rod-like. Formulations having spherical micelles tend to have a low viscosity and exhibit newtonian shear behavior (i.e., viscosity stays constant as a function of shear rate; thus, if easy pouring of product is desired, the solution is less viscous and, as a consequence, it doesn't suspend as well). In these systems, the viscosity increases linearly with surfactant concentration.

Rod micellar solutions are more viscous because movement of the longer micelles is restricted. At a critical shear rate, the micelles align and the solution becomes shear thinning. Addition of salts increases the size of the rod micelles thereof increasing zero shear viscosity (i.e., viscosity when sitting in bottle) which helps suspend particles but also increases critical shear rate (point at which product becomes shear thinning; higher critical shear rates means product is more difficult to pour).

Lamellar dispersions differ from both spherical and rod-like micelles because they can have high zero shear viscosity (because of the close packed arrangement of constituent lamellar droplets), yet these solutions are very shear thinning (readily dispense on pouring). That is, the solutions can become thinner than rod micellar solutions at moderate shear rates.

In formulating liquid cleansing compositions, therefore, there is the choice of using rod-micellar solutions (whose zero shear viscosity, e.g., suspending ability, is not very good and/or are not very shear thinning); or lamellar dispersions (with higher zero shear viscosity, e.g. better suspending, and yet are very shear thinning).

To form such lamellar compositions, however, some compromises have to be made. First, generally higher amounts of surfactant are required to form the lamellar phase. Thus, it is often needed to add auxiliary surfactants and/or salts which are neither desirable nor needed. Second, only certain surfactants will form this phase and, therefore, the choice of surfactants is restricted.

In short, lamellar compositions are generally more desirable (especially for suspending emollient and for providing consumer aesthetics), but more expensive in that they generally require more surfactant and are more restricted in the range of surfactants that can be used.

When rod-micellar solutions are used, they also often require the use of external structurants to enhance viscosity and to suspend particles (again, because they have lower zero shear viscosity than lamellar phase solutions). For this, carbomers and clays are often used. At higher shear rates (as in product dispensing, application of product to body, or rubbing with hands), since the rod-micellar solutions are less shear thinning, the viscosity of the solution stays high and the product can be stringy and thick. Lamellar dispersion based products, having higher zero shear viscosity, can more readily suspend emollients and are typically creamier. Again, however, they are generally more expensive to make (e.g., they are restricted as to which surfactants can be used and often require greater concentration of surfactants).

In general, lamellar phase compositions are easy to identify by their characteristic focal conic shape and oily streak texture while hexagonal phase exhibits angular fan-like texture. In contrast, micellar phases are optically isotropic.

It should be understood that lamellar phases may be formed in a wide variety of surfactant systems using a wide variety of lamellar phase "inducers" as described, for example, in PCT publication, WO 97/05857. Generally, the transition from micelle to lamellar phase is a function of effective average area of headgroup of the surfactant, the length of the extended tail, and the volume of tail. Using branched surfactants or surfactants with smaller headgroups or bulky tails are all effective ways of inducing transitions from rod micellar to lamellar.

U.S. Pat. No. 5,661,189 directed to a detergent composition, teaches an aqueous liquid cleansing and moisturizing composition comprising a surface active agent selected from anionic, nonionic, zwitterionic and cationic surface active agents and mixtures thereof; an benefit agent having a weight average particle size in the range 50 to 500 microns; and a thickening agent. The thickening agent is added to the benefit agent in amount from 1 to 50% wt, based on the benefit agent.

U.S. Pat. No. 5,965,500 for a stable liquid composition comprising high levels of emollients, teaches the use of high foaming aqueous liquid compositions with levels of oil/emollient equal to or in excess of level of surfactant. Good levels of foam can be maintained at such high levels of emollient. In addition to surfactant and emollient, compositions also preferably comprise C12-24 fatty acid and/or cationic polymer.

U.S. Pat. No. 6,174,846 for a liquid composition with enhanced low temperature stability, teaches the use of liquid cleansing compositions in a lamellar phase. Use of minimum amounts of defined polymeric hydrophilic emulsifier in combination with a lamellar phase inducing structurant has been found to enhance both initial viscosity and free thaw (low temperature) viscosity/stability.

U.S. Patent Application Publication Number 2003/018046 for a stable surfactant composition for suspending components teaches free-flowing surfactant composition comprising at least one anionic surface-active agent, an alkanolamide, an electrolyte, and water is described. In particular, the composition is a surfactant composition that has free-flowing non-Newtonian shear thinning properties and the ability to suspend components and is stable under at least one freeze/thaw cycle.

It is to be noted, however, that current spherulite products require improvement in delivering oil to substrates such as skin, hair or wool. Thus, there remains a need to provide enhanced delivery of an oil phase to a substrate such as skin, hair or wool by incorporating the oil into the spherulite formula at a later stage in the manufacturing process, and protecting the oil from excessive emulsification.

There is also a need to enhance the delivery of the oil phase to the skin by incorporating the oil into the spherulite formula at a later stage in the manufacturing process, in conjunction with increased salt concentrations.

BRIEF SUMMARY OF THE INVENTION

Figure 1:
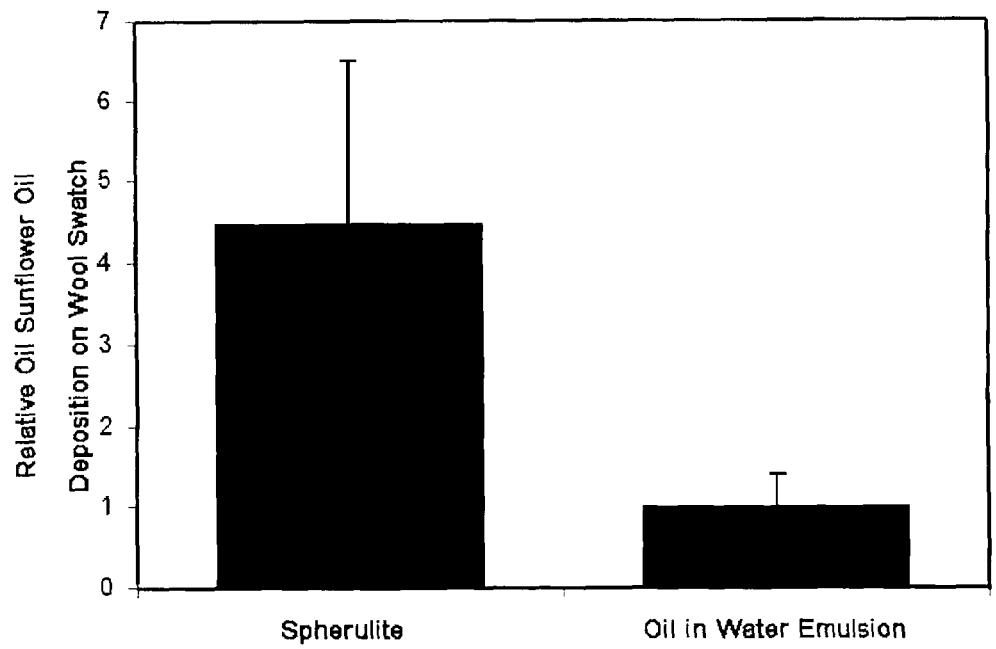
FIG. 1 depicts the effect of surfactant phase structure on sunflower oil deposition: spherulites vs. emulsified oil. At a constant oil concentration of 10 wt % and a constant total surfactant concentration of 10.8%, the spherulite formula delivers approximately 4.5 times more oil to a wool substrate when compared to an oil in water emulsion, $p \leq 0.05$. The compositions are outlined in Table 1.

The invention includes a method of preparing a composition that includes the steps of: (a) premixing a cationic guar gum in water; (b) adding a surfactant component to the premix of (a); (c) adding about 1 to about 3 weight % of salt to the mixture obtained in (b); (d) applying shear to the mixture obtained in (c) at a shear rate not exceeding about 20 sec$^{-1}$ to form a spherulite composition; and (f) mixing an oil phase with the spherulite composition. The resulting composition has a total salt content of about no greater than 6 weight %.

Also included in the invention are compositions comprising a surfactant component, salt and an oil phase, and having a total salt content of about no greater than 6 weight %. The composition is prepared by the process described above.

DETAILED DESCRIPTION OF THE INVENTION

In certain aspects, the invention is directed to a novel approach to enhance the delivery of an oil phase to a substrate such as hair, skin or wool. Aspects of the invention use spherulite technology with selective incorporation of the oil phase after the spherulites are formed. The spherulite material is formed in the presence of salt with shear and slightly acidic pH. This approach takes advantage of the significant reduction in particle diffusion in the spherulite structured body wash formulas.

According to one embodiment of the invention, a spherulite composition may be made by combining a surfactant component, salt and an oil phase wherein:

(I) the surfactant component preferably comprises (based on the final formula of the spherulite composition):
  (a) from about 6 to about 10 weight % sodium trideceth sulfate;
  (b) from about 1.8 to about 3.0 weight % of a structuring agent;
  (c) from about 1.1 to about 3.0 weight % of foam booster;
  (d) water; and
  (e) about 0.2 to about 0.8 weight % of a cationic guar gum;

(II) the salt component is preferably NaCl; and (III) the oil phase preferably comprises up to about 15 weight % of the total composition. Preferably, the oil phase comprises one or more oils selected from the group consisting of vegetable oils, mineral oils, and silicone oils.

Preferably, the spherulite composition is made using sequential steps comprising:
  (a1) premixing the cationic guar gum in water to hydrate and disperse said gum;
  (b1) adding the surfactant component to the (a1) component;
  (c1) adjusting the pH of the (b1) component to be in a range of about 5.5±1;
  (d1) adding from about 1 to about 3 weight % of the salt to the (c1) component while maintaining the salt level at or below about 6 weight %;
  (e1) applying shear to component (d1) to form the spherulite composition at a shear rate preferably not exceeding about 20 sec$^{-1}$;
  (f1) adding the oil phase to the (e1) component with mixing.

Amounts are based on the weight of the total composition. Preferably, the total water content of the spherulite composition is in the range of about 55 to about 80 weight %. In certain embodiments, steps (c1) and (d1) can be reversed.

Portions of the surfactant composition may be found premixed. For example, ingredients (a)-(c) of the surfactant composition are available as MIRACARE SLB-365 surfactant mixture from Rhodia.

Figure 2:
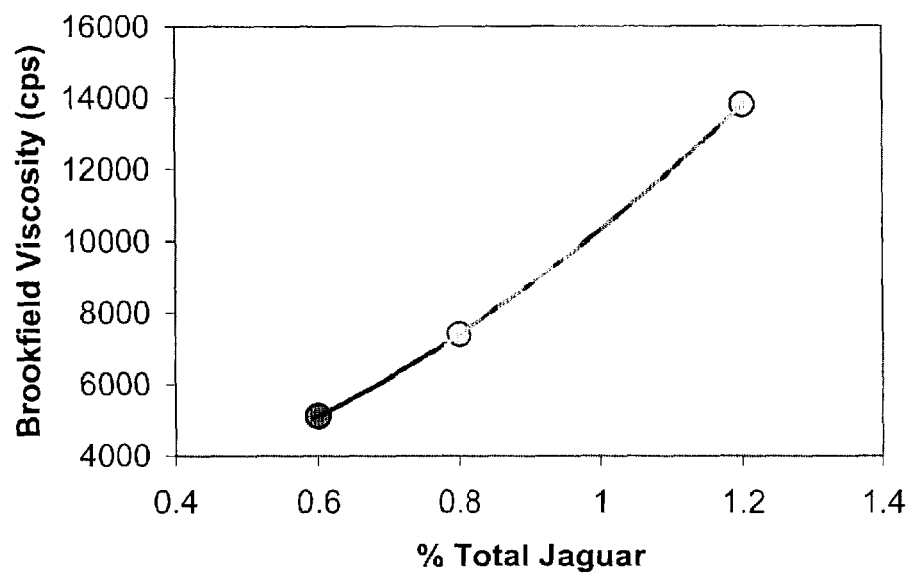
FIG. 2 shows that the viscosity of spherulite compositions containing sunflower oil can be modified through incorporation of a guar gum such as Jaguar S (Rhodia). Increasing the concentration of Jaguar S guar gum significantly increases formula viscosity as measured with a Brookfield Viscometer. The compositions are outlined in Table 6.

Optional ingredients can be included in the spherulite system to control and/or build the viscosity of the final product. For example, instance, a noncationic guar gum (for example, up to about 1 weight % of Jaguar S from Rhodia) can be incorporated into the formula to build viscosity. (Note that FIG. 2 shows that as the total amount of Jaguar S and Jaguar C-17 materials in the formula is increased, then the viscosity of the formula can be significantly increased from about 5,000 to about 13,500 cps, using a Brookfield Viscometer (#5 spindle at 20 rpm)).

One particular embodiment of the invention may be described as a spherulite composition comprising: a surfactant pre-mix which contains less than or equal to about 36 weight % sodium trideceth sulfate, less than or equal to about 10 weight % lauroamphoacetate, and less than or equal to about 6 to 11 weight % cocomonoethanolamide in water. This surfactant premix can be obtained from Rhodia, and is similar to a commercial material available as MIRACARE SLB-365. The exact concentrations of the individual surfactant components can be modified to alter the surfactant concentrations in the final product.

In certain embodiments, about 0.2 to about 0.8 weight %, more preferably about 0.2 to about 0.7 weight %, and most preferably about 0.3 to about 0.5 weight % of a cationic guar gum such as guar hydroxypropyl trimonium chloride ("HPTC") (for example, as sold under the name Jaguar C-17 from Rhodia (Cranberry, N.J.)) may, for example, be added to water in the formulation and mixed until fully hydrated and dispersed. (The additional water in the formulation represents, for example, about 56 to about 58% of the final formula.) The cationic guar gum may be added to the water solution at room temperature or by heating the solution (for example, to a temperature in the range of about 40 to 50 degrees C.), and slowly mixing prior to addition to the surfactant solution.) The surfactant premix may be then diluted into the cationic guar gum/water mixture (Jaguar C-17 (HPTC)/water mix) to yield a mixture which, after completion of forming the final composition, comprises:

(a) preferably about 6 to about 9 weight % and more preferably about 7.35 to about 8.25 weight % sodium trideceth sulfate;

(b) preferably about 1.8 to about 3.0 weight % and more preferably about 2.04 to about 2.29 weight % of a structuring agent (for example, lauroamphoacetate or cocoamidopropyl betaine);

(c) preferably about 1.1 to about 3.0 weight % and more preferably about 1.22 to about 2.52 weight % of a foam booster (for example, cocomonoethanolamide and more particularly where a portion of the cocmonoethanolamide is added to the surfactant solution by heating the solution to about 40 degrees C., and slowly adding melted cocomonoethanolamide);

(d) water (for example, about 52 to about 54 weight % of the surfactant premix); wherein as sequential steps:

(a1) after the surfactant pre-mix and the water containing cationic guar gum are mixed together, the pH is adjusted to be in a range of about 5.5±1;

(b1) preferably about 1 to about 3 weight % and most preferably about 1.5 to about 2.5 weight % of salt is added to the solution (for example, NaCl as added to the formulation dissolved in water as a brine solution (for example, about 25 weight % brine).

(c1) shear is applied to the sample to mix the various components, and to induce the formation of spherulites in the formulation (for example, using a maximum shear rate less than or equal to about 20 sec$^{-1}$).

(d1) an oil phase comprising one or more members selected from the group consisting of vegetable oils (for example, Sunflower Oil and/or Soy Bean Oil) which comprises up to about 15 weight % of the spherulite composition is added to the mixture using simple mixing. The oil phase can be added to the formulation after the spherulites are formed or before the adjustment of the pH and addition of salt to form a stable formula.

An optional ingredient for control of viscosity of the final product, for instance, guar gum (for example Jaguar S from Rhodia) can be incorporated into the formula to build viscosity. The Jaguar S may be added to the water phase according to the above method at the same time as the HPTC (Jaguar C-17), followed by thorough mixing until the Jaguar materials are fully hydrated. One can add the Jaguar S and Jaguar C-17 materials to the water solution by heating the solution to about 40 to about 50 degrees C., and slowly mixing prior to addition to the surfactant solution to enhance dissolution and hydration. Incorporation of a mixture of both Jaguar C-17 and Jaguar S materials can be used to significantly increase formula viscosity. FIG. 2 shows that as the total amount of Jaguar S and Jaguar C-17 materials in the formula is increased, the viscosity of the formula can be significantly increased from about 5,000 to about 13,500 cps, (measurements made using a Brookfield Viscometer (#5 spindle at 20 rpm)).

Other optional ingredients which can be incorporated into the spherulite compositions of the invention include fragrances, antibacterial agents such as triclosan and TCC, antidandruff agents such as climbazole and zinc pyrithione, and other particulates or hydrophobic materials.

The above formulation can be made at room temperature, if all of the cocmonoethanolamide is incorporated into the surfactant pre-mix, or at about 40 to about 50 degrees C. if a portion of the cocomonoethanolamide is added to the water phase. If the formulation is made at about 40 to about 50 degrees C., the batch is cooled to room temperature after addition of the Jaguar C-17 and/or Jaguar S materials to facilitate addition of other components.

In certain embodiments, to maximize the potential for oil delivery to a substrate of the formula, the oil phase may be added after the spherulites are formed, taking advantage of the significant reduction in particle diffusion in the spherulite structured body wash formulas. Table 4 shows that addition of increased amounts of NaCl to the spherulite surfactant system where the oil is added after formation of the spherulites leads to a substantial increase the deposition of the oil phase onto a substrate during washing. This is not observed if the oil is added to the formula before the spherulites are formed.

EXAMPLES

The following Examples are offered as illustrative of the invention and are not to be construed as limitations thereon. In the Examples and elsewhere in the description of the invention, chemical symbols and terminology have their usual and customary meanings. Table 7 is a list of formula components and trade names used in the current examples. In the Examples as elsewhere in this application values for n, m, etc. in formulas, molecular weights and degree of ethoxylation or propoxylation are averages. Temperatures are in degrees C. unless otherwise indicated. The amounts of the components are in weight percents based on the standard described; if no other standard is described then the total weight of the composition is to be inferred. Various names of chemical components include those listed in the *CTFA International Cosmetic Ingredient Dictionary* (Cosmetics, Toiletry and Fragrance Association, Inc., 7$^{th}$ ed. 1997).

A list of formula components and trade names used in the current examples is shown in table 7. All examples were made using the methods described above. AI refers to active level.

Example 1A and 1B

Preliminary experiments using a standard wool binding assay were performed to determine whether changing surfactant phase structure from an oil in water emulsion to a spherulitic phase structure improved the delivery of oil to the skin's surface during washing FIG. 1 and Table 1). Initial experiments showed that at the same oil concentration of 10% and total surfactant concentration of 10.8%, a spherulitic surfactant system delivered approximately 4.5 times more oil the wool substrate compared to an oil in water emulsion formula ($p \leq 0.05$, FIG. 1).

Example 1A

One particular method for making the invention is as follows. Note that the guar hydroxypropyl trimonium chloride ("HPTC") (for example, as sold under the name Jaguar C-17 from Rhodia (Cranberry, N.J.)) is formed as a premix with water and mixed until fully hydrated and dispersed. The additional water in the formulation represents, 62.7 weight % of the final formula. The surfactant pre-mix which contains less than or equal to about 36 weight % sodium trideceth sulfate, less than or equal to about 10 weight % lauroamphoacetate, and less than or equal to about 6 to 11 weight % cocomonoethanolamide in water is selected. This surfactant premix can be obtained from Rhodia, and is similar to a commercial material MIRACARE SLB-365. The exact concentrations of the individual surfactant components can be modified to alter the surfactant concentrations in the final product. The surfactant premix is mixed with the Jaguar C-17 solution to yield a final concentration of the surfactant components as listed in Table 1. The types and amounts of ingredients are listed in Table 1. After the surfactant pre-mix and the water containing HPTC are mixed together, the temperature is increased to 50 degrees C., and the cocomonoethanolamide is added as a melt. The sample is stirred until all the cocomonoethanolamide is completely dispersed. The sunflower oil is then added, followed by mixing, and the formula is cooled to 40 degrees C., at which time a preservative is added. The formula is then cooled to room temperature.

Further sequential steps are
(a1) the pH is adjusted to be 5.2 by adding citric acid;
(b1) 1 weight % NaCl as added to the formulation dissolved in water as a brine solution;
(c1) shear is applied to the sample to mix the various components, maintaining a maximum shear rate less than or equal to 20 sec$^{-1}$; and Note that for subsequent Examples, an optional ingredient for controlling and building viscosity of the final product is used (a non-cationic guar gum, Jaguar S from Rhodia). The Jaguar S is added to the water phase according to the above method at the same time as the HPTC (Jaguar C-17 material), followed by thorough mixing until the Jaguar materials are fully hydrated and dispersed. The Jaguar S and Jaguar C-17 materials are added to the water solution by heating the solution to between 40 to 50 degrees C. (which was done in the Examples but is not necessarily required), and slowly mixing prior to addition to the surfactant solution to enhance dissolution and hydration. (For example, the formulation can be made either at room temperature, if all of the cocmonoethanolamide is incorporated into the surfactant pre-mix, or between 40 and 50 degrees C. if a portion of the cocomonoethanolamide is added to the water phase.) If the formulation is made at between 40 and 50 degrees C., the batch is cooled to room temperature after addition of the Jaguar C-17 and/or Jaguar S materials to facilitate the addition of other components.

In Example 1A, the oil was added before the spherulites were formed. The remainder of the Examples has the addition order noted in the Tables. The oil phase should be added after the spherulites are formed, taking advantage of the significant reduction in particle diffusion in the spherulite structured body wash formulas.

Example 1B

One particular method for making an oil in water emulsion is as follows. A primary phase of water is heated to 80 degrees C., and the hydroxypropylmethyl cellulose (available from Dow Chemical as METHOCEL® E4Ma) is added and mixed until fully dispersed. The decyl glucoside is then added and mixed completely. A second phase is formed by heating the sunflower oil to between 60 and 65 C, to which the acrylate crosspolymer (available as PEMULEN® TR1 from Noveon) is added, followed by dispersal with vigorous mixing. The second phase is then cooled to 60 degrees C., and the lauric acid is added. The second phase is then stirred for 30 minutes. The SLES is then added to the second phase with mixing, then all the additional ingredients for the oil in water emulsion listed in Table 1 are added in the order presented in Table 1. Each ingredient is completely mixed into the formula before the next ingredient is added. The sample is then cooled to below 40 C, and the preservative DMDMH is added.

TABLE 1

Compositions for addition of sunflower oil to a formula which is either a spherulite or oil in water emulsion formula identified in FIG. 1.

| Ingredient | Spherulite | O/W Emulsion |
|---|---|---|
| DI H$_2$O | 62.68 | 45.16 |
| Jaguar C17 | 0.70 | — |
| MIRACARE SLB-365 (48% AI) | 20.42 | — |
| Alkamide C212 | 1.00 | — |
| Sunflower Oil | 10.00 | 10.00 |
| Citric Acid (50% Solution) | 1.00 | — |
| Sodium Chloride (25% Solution) | 4.00 | — |
| METHOCEL ®E4M | — | 0.50 |
| Decyl Glucaside | — | 1.20 |
| PEMULEN ® TR1 | — | 0.50 |
| Lauric Acid | — | 1.00 |
| SLES (36% AI) | — | 30.00 |
| CAP Betaine | — | 8.50 |
| Triethanolamine | — | 0.30 |
| MERQUAT ® Plus 3330 | — | 1.37 |
| MERQUAT ® 150 | — | 0.88 |
| Hampene 100 | — | 0.20 |
| Glydant DMDMH | 0.20 | 0.40 |

Example 2

Experiments were then conducted to determine whether addition of oil before or after formation of the spherulites would modify the deposition of oil on a substrate (Tables 2 and 3). The method described in Example 1 was repeated with the types and amounts of ingredients described in Tables 2 and 3. Interestingly, addition of the oil after formation of the spherulites led to a significant increase in oil deposition. The data in Table 2 suggests that the increased deposition with post addition of oil may be greater at reduced surfactant concentration of 10.8% compared to about 15.6%.

TABLE 2

Effect of surfactant concentration and the order of addition of sunflower oil to a formula either before or after formation of spherulites. Formula compositions are outlined in Table 3.

| % Surfactant | Deposition Pre Mix Oil □g/cm2 | Deposition Post Mix Oil □g/cm2 |
|---|---|---|
| 10.8 | 227 ± 16 | 282 ± 20 |
| 15.6 | 241 ± 8 | 288 ± 61 |
| P≦ | 0.222 | 0.864 |

TABLE 3

Compositions for addition of sunflower oil to a formula either before or after formation of spherulites identified in Table 2.

| Ingredient | 10.8% Surfactant-Pre Mix Oil | 10.8% Surfactant-Post Mix Oil | 15.6% Surfactant-Pre Mix Oil | 15.6% Surfactant-Post Mix Oil |
|---|---|---|---|---|
| DI H$_2$O | 57.7 | 57.69 | 47.91 | 47.5 |
| Versene 100 | 0.21 | 0.2 | 0.5 | 0.2 |
| Jaguar C17 | 0.71 | 0.71 | 0.7 | 0.69 |
| MIRACARE SLB-365 (48% AI) | 20.45 | 20.48 | 29.82 | 31.01 |
| Alkamide C212 | 0.99 | 1 | 0.87 | 0.87 |
| Sunflower Oil | 10.05 | 10.2 | 9.98 | 9.78 |
| Glydant DMDMH | 0.2 | 0.21 | 0.4 | 0.4 |
| Citric Acid (50% Solution) | 0.81 | 0.82 | 0.99 | 0.9 |
| Sodium Chloride (25% Solution) | 8.01 | 8.03 | 7.96 | 7.85 |
| Fragrance | 0.8 | 0.85 | 0.79 | 0.79 |

Example 4

Additional experiments have shown that the structure and stability of the spherulite based systems is dependent of the ionic strength of the aqueous phase. The method described in Example 1 was repeated with the types and amounts of ingredients listed in Tables 4 and 5. Structure and viscosity increases with increase NaCl concentration between the 0% and 3% added salt evaluated. Experiments were conducted to determine whether changing the salt concentration might have an impact on oil deposition on a substrate. Tables 4 and 5 show that addition or NaCl increases the deposition of oil only when the oil is added to the formulas after the spherulites are formed, A clear, and significant-p≦0.02), dose dependent increase in oil deposition is observed between about 1.58 and 2.42 wt % added NaCl. These results were unexpected, and suggest that the efficiency of oil delivery can be further improved by controlling the concentration of salt in the formulation.

TABLE 4

Effect of NaCl concentration and the order of addition of sunflower oil to a formula either before or after formation of spherulites. Formula compositions are outlined in Table 5.

| Weight % Added NaCl | Deposition Pre Add Oil □g/cm2 | Deposition-Post Add Oil □g/cm2 |
|---|---|---|
| 1.58 | 228 ± 42 | 238 ± 23 |
| 2.00 | 257 ± 7 | 252 ± 19 |
| 2.42 | 241 ± 11 | 300 ± 25 |
| P≦ | 0.54 | 0.02 |

TABLE 5

Compositions for addition of sunflower oil to a formula either before or after formation of spherulites identified in Table 4.

| Ingredient | 1.58% NaCl-Pre Mix Oil | 2.00% NaCl-Pre Mix Oil | 2.48% NaCl-Pre Mix Oil | 1.58% NaCl-Post Mix Oil | 2.00% NaCl-Post Mix Oil | 2.48% NaCl-Post Mix Oil |
|---|---|---|---|---|---|---|
| DI H$_2$O | 58.9 | 57.25 | 55.61 | 58.99 | 57.35 | 55.7 |
| Versene 100 | 0.2 | 0.2 | 0.2 | 0.2 | 0.2 | 0.2 |
| Jaguar C17 | 0.7 | 0.7 | 0.7 | 0.71 | 0.71 | 0.71 |
| MIRACARE SLB-365 (48% AI) | 20.77 | 20.77 | 20.77 | 20.8 | 20.8 | 20.8 |
| Alkamide C212 | 1.03 | 1.03 | 1.03 | 1.01 | 1.01 | 1.01 |
| Sunflower Oil | 10.2 | 10.2 | 10.2 | 10.07 | 10.07 | 10.07 |
| Glydant DMDMH | 0.4 | 0.4 | 0.4 | 0.4 | 0.4 | 0.4 |
| Citric Acid (50% Solution) | 0.67 | 0.67 | 0.67 | 0.68 | 0.68 | 0.68 |
| Sodium Chloride (25% Solution) | 6.31 | 7.96 | 9.6 | 6.32 | 7.97 | 9.62 |
| Fragrance | 0.81 | 0.81 | 0.81 | 0.81 | 0.81 | 0.81 |

AI = active level

Example 6

Additional experiments were conducted to determine whether the Brookfield Viscosity (measured with a #5 spindle at 20 rpm) could be modified using a guar instead of significantly changing the salt concentration. The formulas were made by adding the addition Jaguar C-17 and Jaguar S to the water solution at 40 C prior to addition of the surfactant pre-mix.

FIG. 2 shows that the viscosity of the spherulite based shower gel can be significantly modified by the incorporation of small concentrations of guar gums such as Jaguar S and Jaguar C17 materials from (Rhodia).

TABLE 6

Compositions for addition of Jaguar S guar gum to spherulite shower gel formulas containing sunflower oil identified in FIG. 2.

| Formula | 0.6% Jaguar | 0.8% Jaguar | 1.2% Jaguar |
|---|---|---|---|
| DI H$_2$O | 57.28 | 57.08 | 56.68 |
| Versene 100 | 0.2 | 0.2 | 0.2 |
| Jaguar C17 | 0.3 | 0.3 | 0.4 |
| Jaguar S | 0.3 | 0.5 | 0.8 |
| MIRACARE SLB-365 (48% AI) | 20.8 | 20.8 | 20.8 |
| Alkamide C212 | 1.02 | 1.02 | 1.02 |
| Sunflower Oil | 10 | 10 | 10 |
| Glydant DMDMH | 0.4 | 0.4 | 0.4 |
| Citric Acid (50% Solution) | 0.7 | 0.7 | 0.7 |
| Sodium Chloride (25% Solution) | 8.2 | 8.2 | 8.2 |
| Fragrance | 0.8 | 0.8 | 0.8 |

TABLE 7

A list of formula components and trade names used in the current examples.

| Ingredient | Trade/Generic Name |
|---|---|
| Tetrasodium Ethylenediamine Tetra-acetic Acid | Versene 100 |
| Guar Hydroxypropyl Trimonium Chloride | Jaguar C17 |
| Guar Gum | Jaguar S |
| A mixture of Sodiun Tridecethsulfate, Lauroamphoacetate, and Cocomonoethanolamide | MIRACARE SLB-365 |
| Alkamide C212 (Cocomonoethanolamide) | Surfactant System |
| 50 weight % Citric Acid in H$_2$O | Citric Acid (50% AI) |
| 25 weight % NaCl in H$_2$O | Brine (25% AI) |
| DMDMH | Glydant |
| Hydroxypropyl Methylcellulose | METHOCEL ® E4M |
| Acrylates/C10-C30 Alkyl Acrylate Cross Polymer | PEMULEN ® TR1 |
| Sodium Laureth Sulfate (2EO) | SLES (28% AI) |
| Cocamidopropyl Betaine | CAP Betaine |
| Polyquaternium-39 | MERQUAT ® Plus 3330 |
| Polyquaternium-7 | MERQUAT ® 150 |
| Tetrasodium Ethylenediamine Tetra-acetic Acid | Hampene 100 (39% AI) |

The invention claimed is:

1. A method of making a composition comprising:
    (a) premixing a cationic guar gum comprising guar hydroxypropyl trimonium chloride in water;
    (b) adding a surfactant mixture comprising sodium trideceth sulfate, at least one structuring agent selected from lauroamphoacetate or cocamidopropyl betaine, and cocomonoethanolamide to the premix of (a);
    (c) adding about 1 to about 3 weight % of sodium chloride to the mixture obtained in (b) and adjusting the pH of the mixture to about 4.5 to about 6.5;
    (d) applying shear to the mixture obtained in (c) at a shear rate not exceeding about 20 sec$^{-1}$ to form a spherulite composition; and
    (f) mixing an oil phase comprising at least one oil chosen from vegetable oil, mineral oil and silicone oil with the spherulite composition,
    wherein the composition has an added salt content of no greater than 6 weight %.

2. The method of claim 1, wherein the composition further comprises a noncationic guar gum.

3. The method of claim 1, wherein the total water content of the composition is about 55 to about 80 weight %.

4. The method of claim 1 wherein (b) comprises adding a surfactant component that comprises
    (a) about 6 to about 10 weight % sodium trideceth sulfate,
    (b) about 1.8 to about 3.0 weight % lauroamphoacetate, and
    (c) about 1.1 to about 3.0 weight % cocomonoethanolamide.

* * * * *